(12) United States Patent
Svenstrup et al.

(10) Patent No.: US 8,318,761 B2
(45) Date of Patent: Nov. 27, 2012

(54) SUBSTITUTED ARYLSULFONAMIDES AS ANTIVIRAL AGENTS

(75) Inventors: Niels Svenstrup, Kobenhavn S (DK); Holger Zimmermann, Wuppertal (DE); Dagmar Karthaus, Solingen (DE); Andreas Goeller, Wuppertal (DE); Dirk Heimbach, Duesseldorf (DE); Kerstin Henninger, Wuppertal (DE); Dieter Lang, Velbert (DE); Daniela Paulsen, Wuppertal (DE); Bernd Riedl, Wuppertal (DE); Rudolf Schohe-Loop, Wuppertal (DE); Joachim Schuhmacher, Wuppertal (DE); Tobias Wunberg, Hinterbruehl (AT)

(73) Assignee: Aicuris GmbH & Co. KG, Wuppertal (DE)

( * ) Notice: Subject to any disclaimer, the term of this patent is extended or adjusted under 35 U.S.C. 154(b) by 740 days.

(21) Appl. No.: 12/203,793

(22) Filed: Sep. 3, 2008

(65) Prior Publication Data
US 2009/0176842 A1    Jul. 9, 2009

Related U.S. Application Data

(63) Continuation of application No. PCT/EP2007/001620, filed on Feb. 26, 2007.

(30) Foreign Application Priority Data

Mar. 3, 2006    (DE) .................. 10 2006 009 928

(51) Int. Cl.
*A01N 43/40*     (2006.01)
*A61K 31/435*    (2006.01)
*A61K 31/44*     (2006.01)

(52) U.S. Cl. ........................ 514/277; 514/340
(58) Field of Classification Search .................. 514/277, 514/340
See application file for complete search history.

(56) References Cited

U.S. PATENT DOCUMENTS

| | | | |
|---|---|---|---|
| 7,115,612 B2 | 10/2006 | Wunberg et al. |
| 7,115,636 B2 | 10/2006 | Wunberg et al. |
| 2004/0176374 A1 | 9/2004 | Wunberg et al. |
| 2005/0085549 A1 | 4/2005 | Wunberg et al. |

FOREIGN PATENT DOCUMENTS

| | | |
|---|---|---|
| EP | 1 172 361 | 1/2002 |
| WO | WO-99/37291 | 7/1999 |
| WO | WO-01/02350 | 1/2001 |
| WO | WO-02/085869 | 10/2002 |

OTHER PUBLICATIONS

International Preliminary Report on Patentability for PCT/EP2007/001620, mailed on Oct. 16, 2008, 4 pages (English translation only).
International Search Report for PCT/EP02/03858, mailed on Sep. 30, 2002, 3 pages.
Preliminary Amendment from U.S. Appl. No. 10/474,916, filed Feb. 16, 2006.
Notice of Allowance from U.S. Appl. No. 10/474,916, mailed on Mar. 7, 2006.
Notice of Allowance from U.S. Appl. No. 10/486,054, mailed on Feb. 23, 2006.
Cinatl et al., FEMS Microbiology Reviews (2004) 28:59-77.
Chong et al., Abstracts of the 39th Interscience Conference on Antimicrobial Agents and Chemotherapy, Sep. 1999, p. 439.
International Preliminary Examination Report for PCT/EP2007/001620, mailed Jun. 9, 2008, 5 pages.
International Search Report and Written Opinion for PCT/EP2007/001620, mailed Jul. 12, 2007, 12 pages.
Larhed and Hallberg in: Handbook of organopalladium chemistry for organic synthesis, Negishi (ed.), Wiley-Interscience, New York (2002) pp. 1133-1178.
Tykwinski, Angew. Chem. Int. Ed. (2003) 42:1566-1568.
Lischka et al., "Antiviral strategies to combat cytomegalovirus infections in transplant recipients," Current Opinion in Pharmacology (2008) 8:1-8.
AiCuris Press Release, "AiCuris Drug Letermovir (AIC246) meets primary efficacy endpoints in phase 2 for human cytomegalovirus (HCMV) prophylaxis in human blood precursor cell recipients," Feb. 14, 2012, 3 pages.
Tan, "CMV prophylaxis—to do or not to do, that is the question," Nephrol. Dial. Transplant (2006) 21:1757-1761.
Waknine, "FDA Approves Longer Valganciclovir CMV Prophylaxis for Kidney Transplant Patients," WebMD Professional (Aug. 11, 2010) 2 pages.
Wong, "Cytomegalovirus Prophylaxis in Renal Transplant Patients," The Hong Kong Medical Diary (2006) 11(5):14-15.

*Primary Examiner* — Yong Chong
(74) *Attorney, Agent, or Firm* — Morrison & Foerster LLP

(57) ABSTRACT

The invention relates to substituted arylsulfonamides of formula (I) and methods for their preparation as well as their use for the production of medicaments for the treatment and/or prophylaxis of diseases, especially for use as antiviral agents, particularly against cytomegaloviruses.

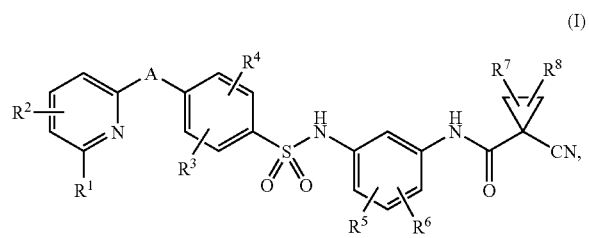

8 Claims, No Drawings

SUBSTITUTED ARYLSULFONAMIDES AS ANTIVIRAL AGENTS

CROSS-REFERENCE TO RELATED APPLICATIONS

This application is a continuation of pending international application PCT/EP2007/001620, filed Feb. 26, 2007, designating US, which claims priority from German patent application DE 10 2006 009 928.1 filed Mar. 3, 2006. The contents of these documents are incorporated herein by reference in their entirety.

BACKGROUND OF THE INVENTION

The invention relates to substituted arylsulfonamides and methods for their preparation as well as their use for the production of medicaments for the treatment and/or prophylaxis of diseases, especially for use as antiviral agents, particularly against cytomegaloviruses.

WO 02/085869 describes substituted arylsulfonamides as antiviral agents, especially against cytomegaloviruses.

SUMMARY OF THE INVENTION

One object of the present invention is to provide new compounds with equal or improved antiviral activity, improved pharmacokinetics, especially a longer half-life and/or improved oral bioavailability, whose metabolic degradation pathways do not differ significantly between human and usual tox-species, such as rat and dog, for the treatment of viral infectious diseases in humans and animals.

Surprisingly it has been found that the substituted arylsulfonamides described in the present invention have antiviral activity, show improved pharmacokinetical properties and that their metabolic degradation pathways do not differ significantly in humans, rats and dogs.

The invention relates to compounds of formula

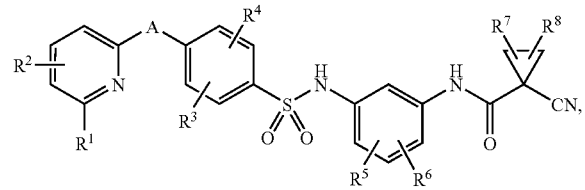

(I)

in which
A represents a group of formula

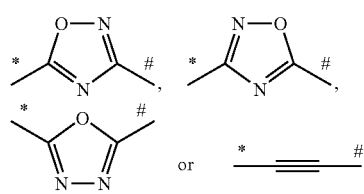

whereby
\* is the linkage site to the carbon atom of the pyridinyl ring, and
\# is the linkage site to the carbon atom of the phenyl ring, $R^1$ represents hydrogen, amino or methylcarbonylamino,
$R^2$ represents hydrogen or halogen,
$R^3$ represents hydrogen, halogen or cyano,
$R^4$ represents hydrogen, halogen or cyano,
$R^5$ represents hydrogen or halogen,
$R^6$ represents hydrogen or halogen,
$R^7$ represents hydrogen, halogen or $C_1$-$C_3$-alkyl,
$R^8$ represents hydrogen, halogen or $C_1$-$C_3$-alkyl,
and their salts, their solvates and the solvates of their salts.

Compounds of the invention are the compounds of formula (I) and their salts, solvates and the solvates of their salts, as well as the compounds encompassed by formula (I) and specified below as exemplary embodiment(s) and their salts, solvates and the solvates of their salts, insofar as the compounds encompassed by formula (I) and mentioned below are not already salts, solvates and solvates of the salts.

The compounds of the invention may, depending on their structure, exist in stereoisomeric forms (enantiomers, diastereomers). The invention accordingly relates to the enantiomers or diastereomers and their respective mixtures. From such mixtures of enantiomers and/or diastereomers it is possible to isolate the stereoisomerically uniform constituents, in a known way.

Where the compounds of the invention can occur in tautomeric forms, the present invention includes all of the tautomeric forms.

Salts preferred for the purposes of the present invention are physiologically acceptable salts of the compounds of the invention. Also included, however, are salts which themselves are not suitable for pharmaceutical applications, but can be used, for example for the isolation or purification of the compounds of the invention.

Physiologically acceptable salts of the compounds of the invention include acid addition salts of mineral acids, carboxylic acids and sulfonic acids, e.g. salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds of the invention also include salts of usual bases, such as, by way of example and preferably, alkali metal salts (e.g. sodium and potassium salts), alkaline earth metal salts (e.g. calcium and magnesium salts) and ammonium salts derived from ammonia or organic amines having 1 to 16 carbon atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates for the purposes of the invention refer to those forms of the compounds of the invention which in solid or liquid state form a complex through coordination with solvent molecules. Hydrates are a special form of the solvates, in which the coordination takes place with water.

Furthermore, the present invention also encompasses prodrugs of the compounds of the invention. The term "prodrugs" encompasses compounds which themselves may be biologically active or inactive, but during their time of residence in the body are converted into compounds of the invention (for example metabolically or hydrolytically).

For the purposes of the present invention the substituents have the following meaning, unless specified otherwise:

Alkyl represents a linear or branched alkyl radical usually having 1 to 3, particularly preferably 1 to 2 carbon atoms, by way of example and preferably methyl, ethyl, n-propyl and isopropyl.

Halogen represents fluorine, chlorine, bromine and iodine, preferably fluorine and chlorine.

In the formula of the group which can stand for A, the end point of the line adjacent to which there is a * or #, does not represent a carbon atom or a $CH_2$-group, but is a component of the bond to the atom to which A is attached.

Preference is given to compounds of formula (I) in which
A represents a group of formula

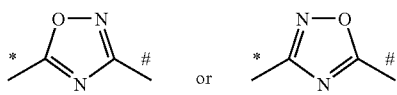

whereby
* is the linkage site to the carbon atom of the pyridinyl ring, and
# is the linkage site to the carbon atom of the phenyl ring,
$R^1$ represents hydrogen, amino or methylcarbonylamino,
$R^2$, $R^3$ and $R^4$ represent hydrogen,
$R^5$ represents hydrogen or halogen,
$R^6$ represents hydrogen or halogen,
$R^7$ and $R^8$ represent hydrogen,
and their salts, their solvates and the solvates of their salts.

Preference is also given to compounds of formula (I), in which
A represents a group of formula

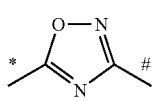

whereby
* is the linkage site to the carbon atom of the pyridinyl ring, and
# is the linkage site to the carbon atom of the phenyl ring,
$R^1$ represents amino or methylcarbonylamino,
$R^2$, $R^3$ and $R^4$ represent hydrogen,
$R^5$ represents hydrogen,
$R^6$ represents hydrogen or halogen,
$R^7$ and $R^8$ represent hydrogen,
and their salts, their solvates and the solvates of their salts.

Preference is also given to compounds of formula (I), in which
A represents a group of formula

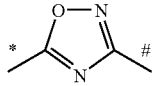

whereby
* is the linkage site to the carbon atom of the pyridinyl ring, and
# is the linkage site to the carbon atom of the phenyl ring.

Preference is also given to compounds of formula (I), in which $R^1$ represents amino.

Preference is also given to compounds of formula (I), in which $R^2$ represents hydrogen.

Preference is also given to compounds of formula (I), in which $R^3$ represents hydrogen.

Preference is also given to compounds of formula (I), in which $R^4$ represents hydrogen.

Preference is also given to compounds of formula (I), in which $R^5$ represents hydrogen.

Preference is also given to compounds of formula (I), in which $R^6$ represents fluorine.

Preference is also given to compounds of formula (I), in which $R^5$ represents hydrogen and $R^6$ represents fluorine.

Preference is also given to compounds of formula (I), in which $R^7$ represents hydrogen.

Preference is also given to compounds of formula (I), in which $R^8$ represents hydrogen.

The radical definitions given specifically in the respective combinations and preferred combinations of radicals are also replaced as desired by radical definitions of another combination, irrespective of the particular combinations of the radicals given.

Very particular preference is given to combinations of two or more of the above-mentioned preference ranges.

The invention further relates to a method for preparing the compounds of formula (I), whereby compounds of formula

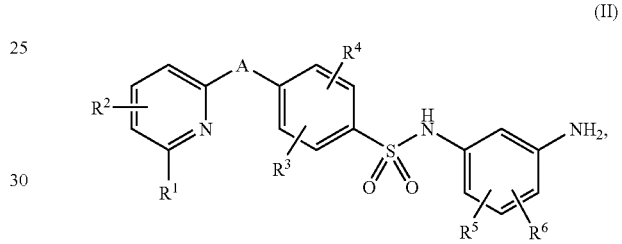

in which
A, $R^1$, $R^2$, $R^3$, $R^4$, $R^5$ and $R^6$ have the meaning indicated above,
are reacted with compounds of formula

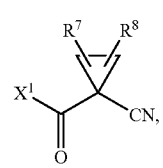

in which
$R^7$ and $R^8$ have the meaning indicated above, and
$X^1$ represents halogen, preferably chlorine or bromine, or hydroxy.

Provided $X^1$ represents halogen, the reaction in general takes place in inert solvents, in the presence of a base, preferably in a temperature range from 0° C. to 40° C. under atmospheric pressure.

Examples of inert solvents include halogenated hydrocarbons such as methylenechloride, trichloromethane or 1,2-dichloroethane, ethers such as dioxane, tetrahydrofuran or 1,2-dimethoxyethane, or other solvents such as acetone, dimethylformamide, dimethylacetamide, 2-butanone or acetonitrile, preference is given to tetrahydrofuran or methylenechloride.

Examples of bases include alkali metal carbonates, such as cesium carbonate, sodium or potassium carbonate, or organic bases such as trialkylamines, e.g. triethylamine or diisopropylethylamine, or N-methylmorpholine, N-methylpiperidine, 4-dimethylaminopyridine or pyridine, preference is given to diisopropylethylamine.

Provided X¹ represents hydroxy, the reaction in general takes place in inert solvents, in the presence of dehydrating reagents, where appropriate in the presence of a base, preferably in a temperature range from 0° C. to room temperature under atmospheric pressure.

Examples of suitable dehydrating reagents hereby include carbodiimides such as N,N'-diethyl-, N,N'-dipropyl-, N,N'-diisopropyl-, N,N'-dicyclohexylcarbodiimide, N-(3-dimethylaminoisopropyl)-N'-ethylcarbodiimide hydrochloride (EDC) (where appropriate in the presence of pentafluorophenol (PFP)), N-cyclohexylcarbodiimide-N'-propyloxymethyl polystyrene (PS-carbodiimide) or carbonyl compounds such as carbonyldiimidazole, or 1,2-oxazolium compounds such as 2-ethyl-5-phenyl-1,2-oxazolium-3-sulfate or 2-tert-butyl-5-methylisoxazolium perchlorate, or acylamino compounds such as 2-ethoxy-1-ethoxycarbonyl-1,2-dihydroquinoline, or propanephosphonic anhydride, or isobutyl chloroformate, or bis(2-oxo-3-oxazolidinyl)phosphoryl chloride, or benzotriazolyloxy-tri(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), or 1-hydroxybenztriazole (HOBt) or benzotriazol-1-yloxytris-(dimethylamino)phosphonium hexafluorophosphate (BOP), or mixtures of these, with bases. Preferably the condensation is carried out with HATU.

Examples of bases include alkali metal carbonates, such as for example sodium or potassium carbonate, or hydrogen carbonate, or organic bases such as trialkylamines, e.g. triethylamine or diisopropylethylamine, or N-methylmorpholine, N-methylpiperidine or 4-dimethylaminopyridine, preference is given to diisopropylethylamine.

Examples of inert solvents include halogenated hydrocarbons such as dichloromethane or trichloromethane, hydrocarbons such as, for example, benzene, or nitromethane, dioxane, dimethylsulfoxide, dimethylformamide, acetonitrile, tetrahydrofuran, or hexamethylphosphoric acid triamide, or mixtures of the solvents, particular preference is given to dichloromethane, tetrahydrofuran or dimethylformamide.

The compounds of formula (III) are known or can be synthesized by known methods from the corresponding starting materials.

The compounds of formula (II) are known or can be prepared by reacting compounds of formula (IV)

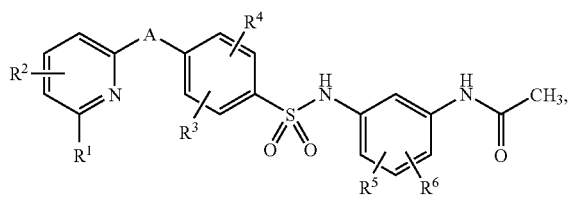

in which
A, R¹, R², R³, R⁴, R⁵ and R⁶ have the meaning indicated above,
with an acid.

The reaction in general takes place in polar solvents, preferably in a temperature range from room temperature to the reflux of the solvent under atmospheric pressure.

Examples of acids include hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid or trifluoroacetic acid, particular preference is given to hydrochloric acid.

Examples of polar solvents include alcohols such as methanol, ethanol, n-propanol, isopropanol, n-butanol or tert-butanol, or tetrahydrofuran, dioxane or acetic acid, or mixtures of the solvents or a mixture of solvent and water, particular preference is given to ethanol.

The compounds of formula (IV) are known or can be prepared by, according to method
[A] reacting compounds of formula (Va)

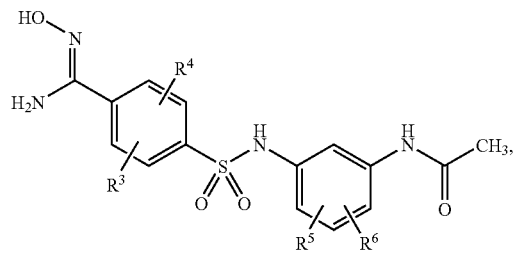

in which
R³, R⁴, R⁵ and R⁶ have the meaning indicated above,
with compounds of formula (VIa)

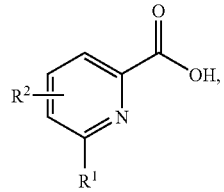

in which
R¹ and R² have the meaning indicated above,
to compounds of formula (IVa)

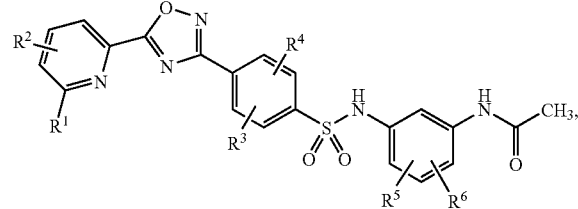

in which
R¹, R², R³, R⁴, R⁵ and R⁶ have the meaning indicated above,
or
[B] reacting compounds of formula (Vb)

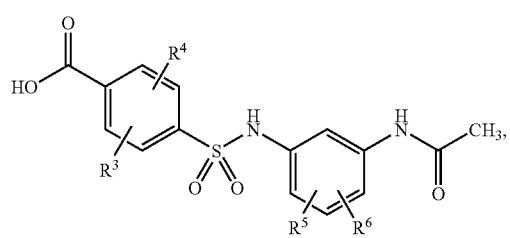

in which
R³, R⁴, R⁵ and R⁶ have the meaning indicated above,
with compounds of formula

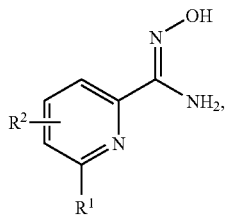

(VIb)

in which
R¹ and R² have the meaning indicated above,
to compounds of formula

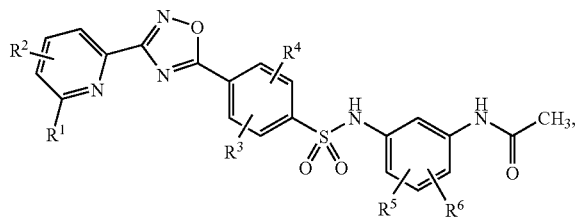

(IVb)

in which
R¹, R², R³, R⁴, R⁵ and R⁶ have the meaning indicated above,
or

[C] in the first stage reacting compounds of formula (Vb) with compounds of formula

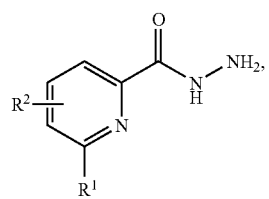

(VIc)

in which
R¹ and R² have the meaning indicated above,
and in the second stage with phosphorous oxychloride, to compounds of formula

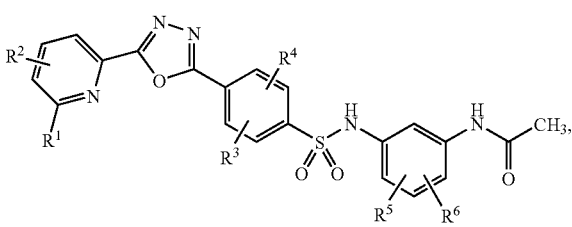

(IVc)

in which
R¹, R², R³, R⁴, R⁵ and R⁶ have the meaning indicated above, or
[D] reacting compounds of formula

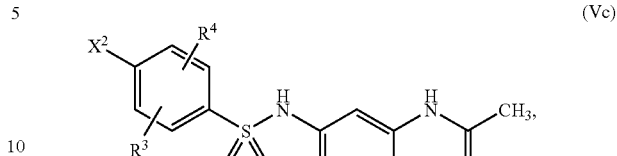

(Vc)

in which
R³, R⁴, R⁵ and R⁶ have the meaning indicated above, and
X² represents halogen, preferably iodine or bromine,
with compounds of formula

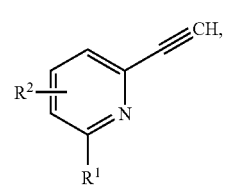

(VId)

in which
R¹ and R² have the meaning indicated above,
to compounds of formula (IVd)

in which
R¹, R², R³, R⁴, R⁵ and R⁶ have the meaning indicated above.

During the synthesis the amino group of R¹ is where appropriate protected with a protecting group known to a man of the art, such as e.g. acyl, which is removed after the synthesis under conditions known to a man of the art.

The compounds of formulas (IVa), (IVb), (IVc), and (IVd) together form the compounds of formula (IV).

The reaction according to method [A], [B] and the first stage of method [C] in general takes place in inert solvents in the presence of dehydrating reagents, preferably in a temperature range from room temperature to 100° C. under atmospheric pressure.

Examples of inert solvents include hydrocarbons such as benzene or toluene, or other solvents such as dioxane, dimethylformamide, dimethylsulfoxide or acetonitrile, or mixtures of the solvents, particular preference is given to dimethylformamide.

Examples of dehydrating reagents include carbodiimides such as N,N'-diethyl-, N,N'-dipropyl-, N,N'-diisopropyl-, N,N'-dicyclohexylcarbodiimide, N-(3-dimethylaminoisopropyl)-N'-ethylcarbodiimide hydrochloride (EDC) (where appropriate in the presence of pentafluorophenol (PFP)), N-cyclohexylcarbodiimide-N'-propyloxymethyl polystyrene (PS-carbodiimide) or carbonyl compounds such as carbonyldiimidazole, or 1,2-oxazolium compounds such as 2-ethyl-5-phenyl-1,2-oxazolium-3-sulfate or 2-tert-butyl-5-methyl-isoxazolium perchlorate, or acylamino compounds such as 2-ethoxy-1-ethoxycarbonyl-1,2-dihydroquinoline, or propanephosphonic anhydride, or isobutyl chloroformate, or bis(2-oxo-3-oxazolidinyl)phosphoryl chloride or benzotriazolyloxy-tri(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), or 1-hydroxybenztriazole (HOBt) or benzotriazol-1-yloxytris(dimethylamino)phosphonium hexafluorophosphate (BOP), or mixtures of these, with bases. Particular preference is given to carbonyldiimidazole.

The reaction of the second stage according to method [C] in general takes place in inert solvents, preferably in a temperature range from 50° C. to 100° C. under atmospheric pressure. It is also possible to use mixtures of the solvents, a mixture of solvent and $POCl_3$ or pure $POCl_3$.

Examples of inert solvents include hydrocarbons such as benzene or toluene, or other solvents such as dioxane, dimethylsulfoxide, dimethylformamide or acetonitrile, or mixtures of the solvents, particular preference is given to dioxane and/or dimethylformamide.

The reaction according to method [D] in general takes place under Sonogashira reaction conditions under argon in inert and degased solvents, in the presence of a catalyst, where appropriate in the presence of an additive reagent, in the presence of a base, and where appropriate triphenylphosphine, preferably in a temperature range from room temperature to the reflux of the solvent under atmospheric pressure (R. R. Tykwinski, Angew. Chem. Int. Ed. 2003, 42, 1566-1568, K. Sonogashira in Handbook of organopalladium chemistry for organic synthesis (Ed. E.-I. Negishi), 1133-1178 Wiley-Interscience, New York (2002)).

Examples of catalysts include palladium catalysts usual for Sonogashira reaction conditions, preference is given to catalysts such as for example tri(dibenzylideneacetone)dipalladium, dichlorobis(triphenylphosphine)palladium, tetrakistriphenylphosphinepalladium(0), palladium(II)-acetate, 1,1'-bis[(biphenylphosphino)ferrocene]palladium-II-chloride (1:1) complex with dichloromethane.

Examples of additive reagents include copper(I)-iodide and triphenylphosphine.

Examples of bases include amine bases such as triethylamine.

Examples of inert solvents include ethers such as dioxane, tetrahydrofuran or 1,2-dimethoxyethane, hydrocarbons such as benzene, xylene or toluene, or other solvents such as nitrobenzene, dimethylformamide, dimethylacetamide, dimethylsulfoxide or N-methylpyrrolidone, preference is given to solvents such as e.g. dimethylformamide, dimethylacetamide, dimethylsulfoxide or 1,2-dimethoxyethane.

The compounds of formulae (VIa), (VIb), (VIc) and (VId) are known or can be synthesized by known methods from the corresponding starting materials.

The compounds of formulae (Va), (Vb) and (Vc) are known or can be prepared by reacting compounds of formula

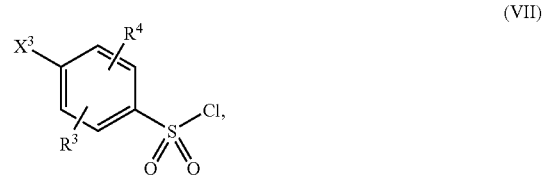

(VII)

in which
$R^3$ and $R^4$ have the meaning indicated above, and
$X^3$ represents halogen, preferably iodine or bromine, hydroxycarbonyl or cyano,
with compounds of formula

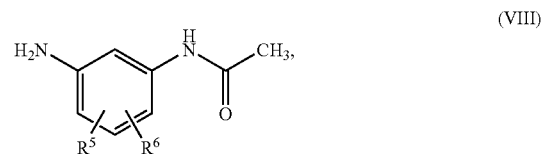

(VIII)

in which
$R^5$ and $R^6$ have the meaning indicated above.

The reaction in general takes place in inert solvents, in the presence of a base, preferably in a temperature range from 0° C. to 40° C. under atmospheric pressure.

Examples of inert solvents include alcohols such as methanol, ethanol, n-propanol, iso-propanol, n-butanol or tert-butanol, or tetrahydrofuran, acetone, dioxane or pyridine, or mixtures of the solvents or a mixture of solvent and water, particular preference is given to tetrahydrofuran or iso-propanol with a little water.

Examples of bases include sodium acetate, potassium acetate, sodium carbonate, potassium carbonate or amine bases such as triethylamine or diisopropylethylamine, particular preference is given to sodium acetate.

The compounds of formulae (VII) and (VIII) are known or can be synthesized by known methods from the corresponding starting materials.

In an alternative method the compounds of formula (IV) can be prepared in a different order of coupling the synthetic building blocks.

The preparation of the compounds of the invention can be illustrated with the following synthesis schemes.

Synthesis scheme 1:

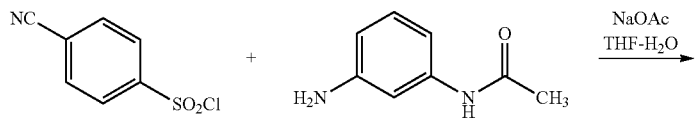

-continued
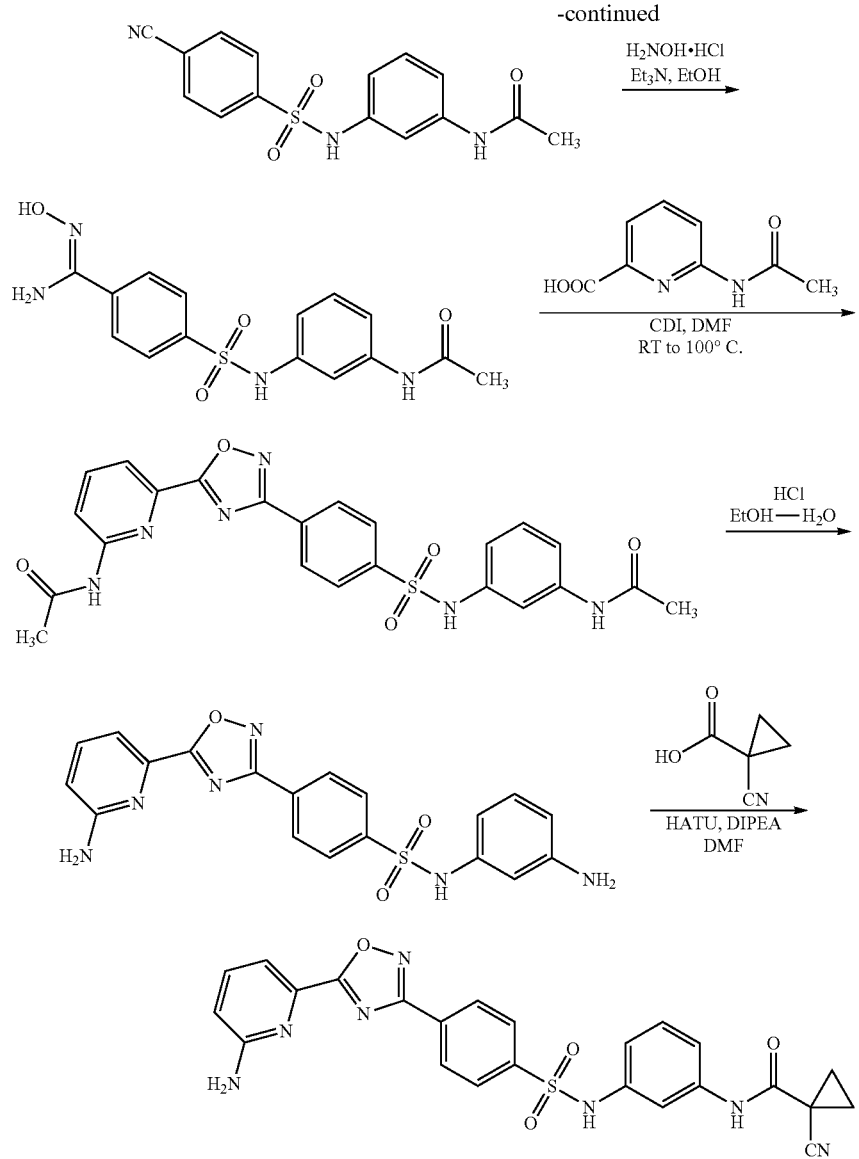
Synthesis scheme 2:
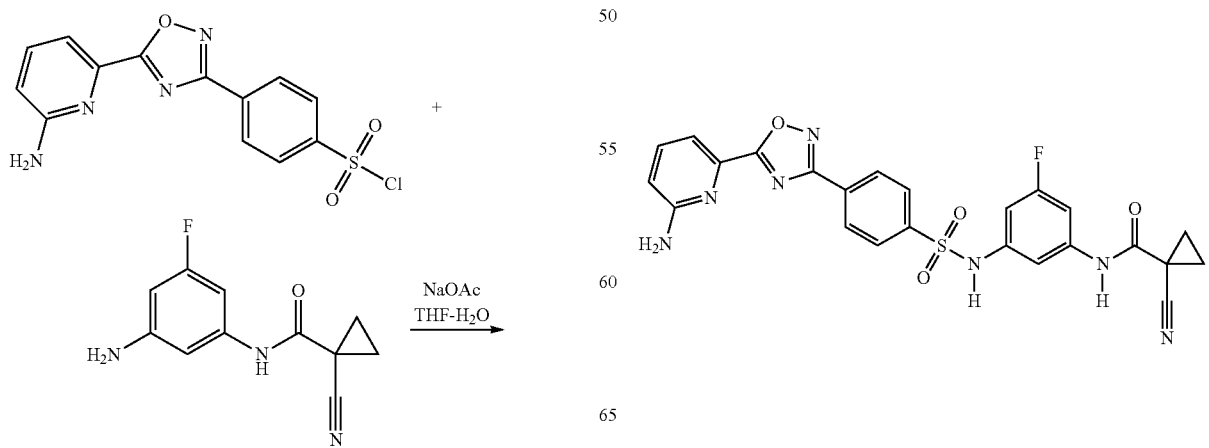

Synthesis scheme 3:
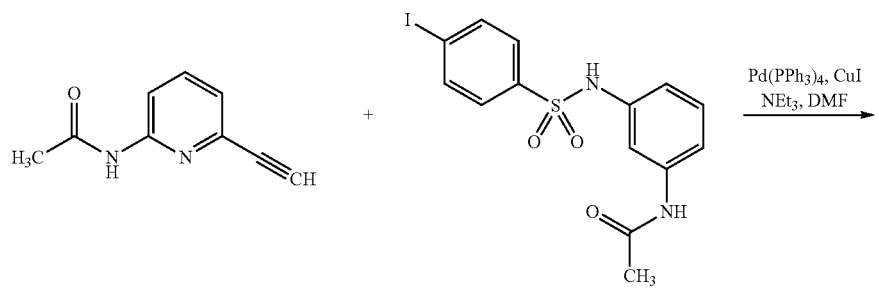
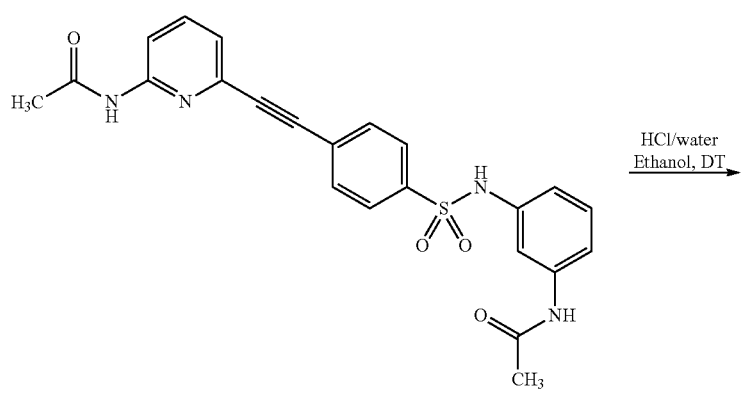
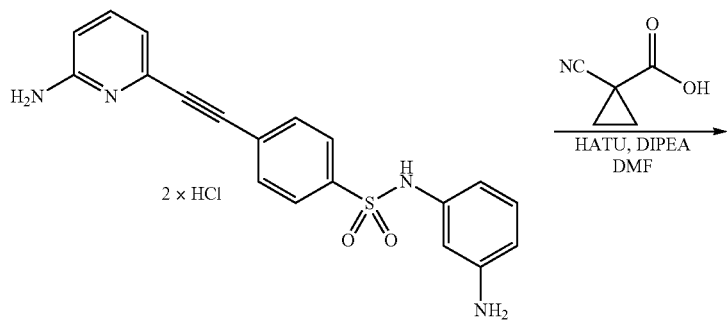
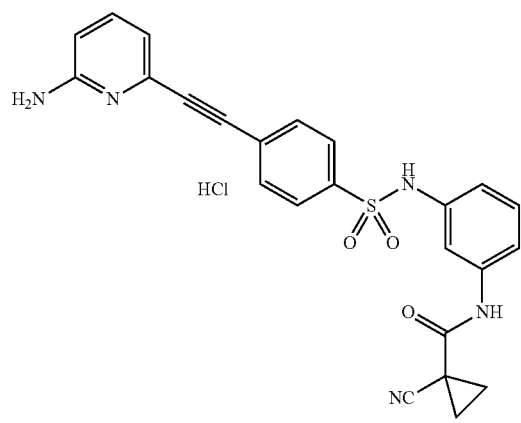

Synthesis scheme 4:

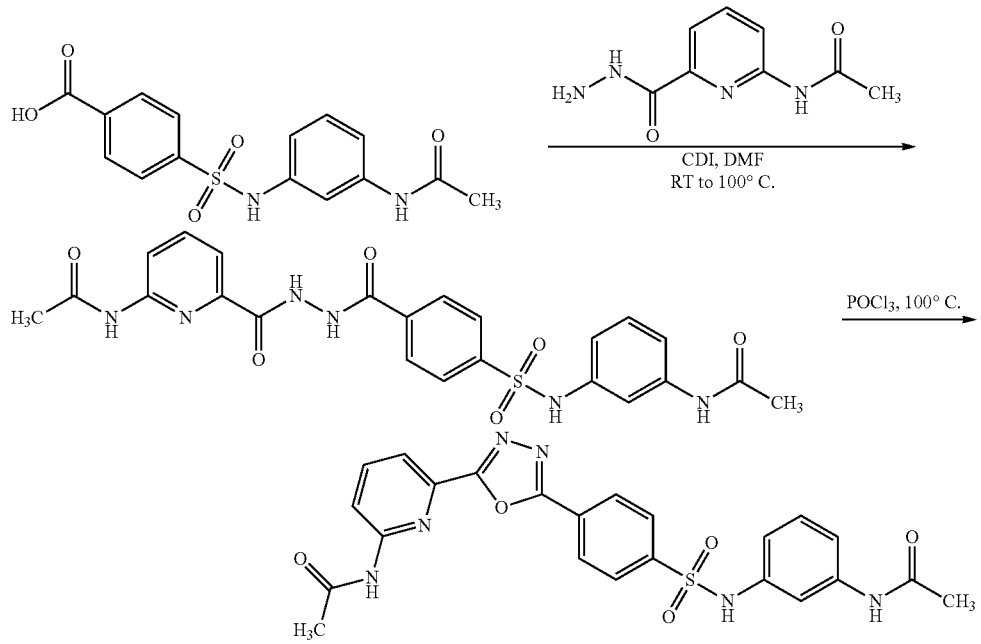

The compounds of the invention show a surprising range of effects which could not have been predicted. They show an antiviral activity on representatives of the group of herpes viridae (herpes viruses), in particular on cytomegaloviruses (CMV) and especially on the human cytomegalovirus (HCMV).

Areas of indication which may be mentioned by way of example are:
1) Treatment and prophylaxis of HCMV infections in AIDS patients (retinitis, pneumonitis, gastrointestinal infections).
2) Treatment and prophylaxis of cytomegalovirus infections in bone-marrow and organ transplant patients who develop often life-threatening HCMV pneumonitis or encephalitis, as well as gastrointestinal and systemic HCMV infections.
3) Treatment and prophylaxis of HCMV infections in neonates and infants.
4) Treatment of an acute HCMV infection in pregnant women.
5) Treatment of an HCMV infection in immunosuppressed patients during cancer and cancer therapy.
6) Treatment of HCMV-positive cancer patients with the aim of reducing HCMV-mediated tumor progression (cf. J. Cinatl, et al., *FEMS Microbiology Reviews* 2004, 28, 59-77).

The present invention further relates to the use of the compounds of the invention for the treatment and/or prophylaxis of diseases, in particular of infections with viruses, especially the afore-mentioned viruses, and of the infectious diseases caused thereby. A viral infection means hereinafter both an infection with a virus and a disease caused by an infection with a virus.

The present invention further relates to the use of the compounds of the invention for the treatment and/or prophylaxis of diseases, especially of the aforementioned diseases.

The present invention further relates to the use of the compounds of the invention for the production of a medicament for the treatment and/or prophylaxis of diseases, especially of the aforementioned diseases.

The compounds of the invention are preferably used for the production of medicaments which are suitable for the prophylaxis and/or treatment of infections with a representative of the group of herpes viridae, in particular a cytomegalovirus, especially the human cytomegalovirus.

The present invention further relates to a method for the treatment and/or prophylaxis of diseases, especially the afore-mentioned diseases, using an antivirally effective amount of the compounds of the invention.

The present invention further relates to medicaments comprising at least one compound of the invention and at least one or more further active ingredients, in particular for the treatment and/or prophylaxis of the afore-mentioned diseases. Suitable active ingredients for the combination which may be mentioned by way of example and preferably, are: antiviral active ingredients such as valganciclovir, ganciclovir or aciclovir.

The compounds of the invention may act systemically and/or locally. For this purpose they can be administered in a suitable way, such as, for example, orally, parenterally, pulmonarily, nasally, sublingually, lingually, buccally, rectally, dermally, transdermally, conjunctivally, oticaly, topically or as implant or stent.

For these administration routes the compounds of the invention can be administered in suitable administration forms.

Suitable for oral administration are administration forms which function according to the prior art and deliver the compounds of the invention rapidly and/or in modified manner and which comprise the compounds of the invention in crystalline and/or amorphicized and/or dissolved form, such as, e.g., tablets (uncoated or coated tablets, for example having coatings which are resistant to gastric juice or dissolve with a delay or are insoluble and control the release of the compound of the invention), tablets or films/wafers which disintegrate rapidly in the oral cavity, films/lyophilisates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g. intramuscular, subcutaneous, intracutaneous, percutaneous, or intraperitoneal). Administration forms suitable for parenteral administration are, inter alia, preparations for injection and infusion in the form of solutions, suspensions, emulsions, lyophilisates or sterile powders.

Examples suitable for the other administration routes include pharmaceutical forms for inhalation (inter alia powder inhalers, nebulizers), nasal drops, solutions, sprays; tablets, films/wafers or capsules, which can be administered lingually, sublingually or buccally, suppositories, preparations for ears or eyes, vaginal capsules, aqueous suspensions (lotions, shaking mixtures), lipophilic suspensions, ointments, creams, transdermal therapeutic systems, milk, pastes, foams, dusting powders, implants or stents.

The compounds of the invention can be converted into the stated administration forms. This can take place in a manner known per se by mixing with inert, non-toxic, pharmaceutically acceptable excipients. These excipients include, inter alia, carriers (for example microcrystalline cellulose, lactose, mannitol), solvents (e.g. liquid polyethylene glycols), emulsifiers and dispersants or wetting agents (for example sodium dodecyl sulfate, polyoxysorbitan oleate), binders (for example polyvinylpyrrolidone), synthetic and natural polymers (e.g. albumin), stabilizers (e.g. antioxidants such as ascorbic acid), colors (for example inorganic pigments such as iron oxides) or taste- and/or odor-corrigents.

The present invention further relates to medicaments which comprise at least one compound of the invention, usually together with one or more inert, non-toxic, pharmaceutically acceptable excipients, as well as to their use for the afore-mentioned purposes.

It has generally proved advantageous to administer on intravenous administration amounts of about 0.001 to 10 mg/kg, preferably about 0.01 to 5 mg/kg, of body weight to achieve effective results, and the dosage on oral administration is about 0.01 to 25 mg/kg, preferably 0.1 to 10 mg/kg, of body weight.

It may nevertheless be necessary where appropriate to deviate from the amounts mentioned, specifically as a function of body weight, administration route, individual response to the active ingredient, type of preparation and time or interval over which administration takes place. Thus it may be sufficient in some cases to make do with less than the afore-mentioned minimum amount, whereas in other cases the upper limit mentioned must be exceeded. In the event of an administration of larger amounts it may be advisable to divide these into a plurality of individual doses over the day.

The percentage data in the following tests and examples are percentages by weight unless otherwise indicated; parts are parts by weight. Solvent ratios, dilution ratios and concentration data of liquid/liquid solutions are in each case based on volume.

DETAILED DESCRIPTION OF PREFERRED EMBODIMENTS

A. Examples

Abbreviations

Boc tert-butoxycarbonyl
$CDCl_3$ deuterochloroform
conc. concentrated
DCI direct chemical ionization (in MS)
DCM dichloromethane
DIEA N,N-diisopropylethylamine
DMSO dimethylsulfoxide
DMF N,N-dimethylformamide
EDC N-(3-dimethylaminoisopropyl)-N'-ethylcarbodiimide hydrochloride
EE ethyl acetate (acetic acid ethyl ester)
EI electron impact ionization (in MS)
ESI electrospray ionization (in MS)
Fmoc 9-fluorenylmethoxycarbonyl
h hour
HPLC high pressure, high performance liquid chromatography
HV high vacuum
LC-MS coupled liquid chromatography-mass spectroscopy
LDA lithium diisopropylamide
min Minutes
MS mass spectroscopy
MTBE methyl tert-butyl ether
NMR nuclear magnetic resonance spectroscopy
Pd—C palladium on carbon
PyBOP 1-benzotriazolyloxytripyrrolidinophosphonium hexafluorophosphate
RP-HPLC reverse phase HPLC
$R_t$ retention time (in HPLC)
sat. saturated
THF tetrahydrofuran General LC-MS and HPLC Methods:

Method 1 (LC-MS): MS instrument type: Micromass ZQ, HPLC instrument type: HP 1100 series; UV DAD; column: Phenomenex Synergi 2μ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 210 nm.

Method 2 (LC-MS): Instrument: Micromass Quattro LCZ with HPLC Agilent series 1100; column: Phenomenex Synergi 2μ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 208-400 nm.

Method 3 (LC-MS): MS instrument type: Micromass ZQ; HPLC instrument type: Waters Alliance 2795; column: Phenomenex Synergi 2μ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 210 nm.

Method 4 (LC-MS): Instrument: Micromass Platform LCZ with HPLC Agilent series 1100; column: Thermo Hypersil GOLD 3μ 20 mm×4 mm; eluent A: 1 l of water+0.5 ml of 50% formic acid, eluent B: 1 l of acetonitrile+0.5 ml of 50% formic acid; gradient: 0.0 min 100% A→0.2 min 100% A→2.9 min 30% A→3.1 min 10% A→5.5 min 10% A; oven: 50° C.; flow rate: 0.8 ml/min; UV detection: 210 nm.

Method 5 (HPLC): Instrument: HP 1100 with DAD detection; column: Kromasil RP-18, 60 mm×2 mm, 3.5 μm; eluent A: 5 ml of perchloric acid/l of water, eluent B: acetonitrile; gradient: 0 min 2% B, 0.5 min 2% B, 4.5 min 90% B, 9 min 90% B, 9.2 min 2% B, 10 min 2% B; flow rate: 0.75 ml/min; oven 30° C.; UV detection: 210 nm.

Method 6 (HPLC): Instrument: HP 1100 with DAD detection; column: Kromasil RP-18, 60 mm×2 mm, 3.5 μm; eluent A: 5 ml of perchloric acid/l of water, eluent B: acetonitrile; gradient: 0 min 2% B, 0.5 min 2% B, 4.5 min 90% B, 6.5 min 90% B, 6.7 min 2% B, 7.5 min 2% B; flow rate: 0.75 ml/min; oven 30° C.; UV detection: 210 nm.

Method 7 (LC/MS): MS instrument type: Micromass ZQ; HPLC instrument type: HP 1100 series; UV DAD; column: Phenomenex Gemini 3μ 30 mm×3.00 mm; eluent A: 1 of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 210 nm.

Starting Compounds

Example 1A 4-(Benzylthio)benzonitrile

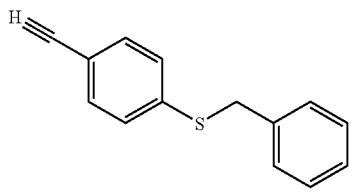

Sodium hydride (5 g of a 60% dispersion in oil) is washed with hexane and dried under vacuum. The residue is slurried in dry DMF (100 ml) at 0° C. and benzyl mercaptan (14.82 g) is added dropwise over 30 min. The reaction mixture is subsequently stirred for 30 min at room temperature. 4-Fluorobenzonitrile (14.45 g) is added cautiously and the reaction mixture is stirred until the starting material has reacted completely (monitoring by HPLC, about 3 h). The reaction mixture is poured onto ice water (400 ml) and stirred for 5 min. The product is collected by filtration, washed with water (three times) and dried on the filter. The crude product is recrystallized from cyclohexane, collected by filtration and washed with petroleum ether and dried. 23.04 g (86% of theory) of product are obtained.

LC-MS (Method 1): $R_t$=2.85 min
MS (ESI): m/z=226 [M+H]$^+$

Example 2A 4-(Benzylthio)-N'-hydroxybenzocarboximidamide

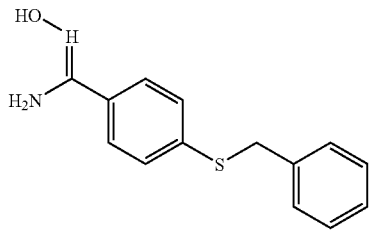

4-(Benzylthio)benzonitrile (23.00 g) and hydroxylamine hydrochloride (10.66 g) are provided in dry ethanol (10 ml) and triethylamine (17 ml) is added. The reaction mixture is first stirred for 30 min at 50° C. and then heated under reflux for 2 h. Subsequently, water is added until the solution becomes turbid. The reaction mixture is cooled to room temperature and the resulting solid is collected by filtration. The solid is washed with water and subsequently dried at 85° C. in a drying oven. The crude product is recrystallized from n-butanol, the crystalline product is collected by filtration, washed with diethylether and dried at 65° C. in a drying oven. 23.40 g (88% of theory) of product are obtained as a solid.

LC-MS (Method 1): $R_t$=1.79 min
MS (ESI): m/z=229 [M+H]$^+$

Example 3A

N-(6-{3-[4-(Benzylthio)phenyl]-1,2,4-oxadiazol-5-yl}pyridin-2-yl)acetamide

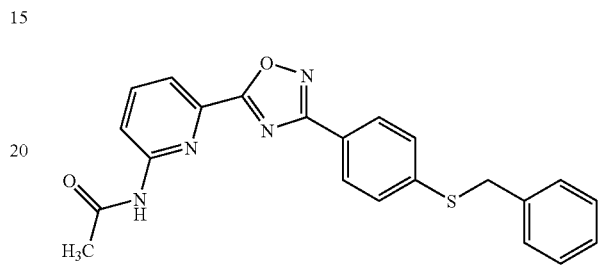

1,1-Carbonyldiimidazole (15.16 g) is added slowly in small portions to 6-acetamidopyridine-2-carboxylic acid (16.84 g) in dry DMF (75 ml) (evolution of gas). The resulting solution is stirred at room temperature for 1.5 h. Then 4-(benzylthio)-N'-hydroxybenzocarboximidamide (23.00 g) is added and the reaction mixture is stirred at room temperature until the starting material has reacted completely (about 3 h). The reaction mixture is heated to 100° C. and stirred for 2 h. Water is subsequently added until the solution becomes slightly turbid and the reaction mixture is cooled to room temperature. The crude product is collected by filtration, washed three times with water and dried in a drying oven at 65° C. 24.42 g (67% of theory) of product are obtained as a solid.

LC-MS (Method 1): $R_t$=2.98 min
MS (ESI): m/z=403 [M+H]$^+$
$^1$H-NMR (400 MHz, DMSO-$d_6$): δ=10.96 (s, 1H), 8.38 (d, 1H), 8.08 (t, 1H), 8.02-7.95 (m, 3H), 7.53 (d, 2H), 7.43 (d, 2H), 7.35-7.21 (m, 3H), 4.36 (s, 2H), 2.15 (s, 3H).

Example 4A

6-{3-[4-(Benzylthio)phenyl]-1,2,4-oxadiazol-5-yl}pyridin-2-amine Hydrochloride

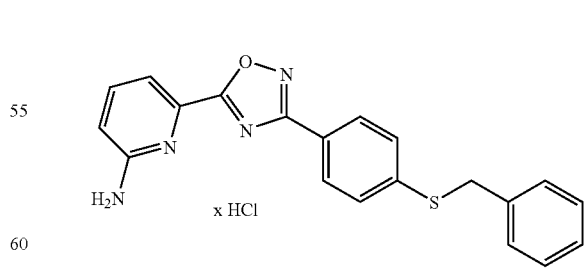

Water (50 ml) and concentrated hydrochloric acid (50 ml) are added to N-(6-{3-[4-(benzylthio)phenyl]-1,2,4-oxadiazol-5-yl}pyridin-2-yl)acetamide (40.55 g) in ethanol (150 ml). The reaction mixture is heated under reflux until the starting material has reacted completely (about 3 h) and subsequently cooled to room temperature. The solid is collected by filtration, washed three times with ethanol and dried in a vacuum oven at 80° C. 36.60 g (92% of theory) of product are obtained as a solid.

LC-MS (Method 2): $R_t$=2.76 min

MS (ESI): m/z=361 [M+H]$^+$ $^1$H-NMR (400 MHz, DMSO-d$_6$): δ=7.95 (d, 2H), 7.73 (t, 1H), 7.53 (d, 2H), 7.51 (m, 1H), 7.42 (d, 2H), 7.30 (t, 2H), 7.25 (m, 1H), 6.85 (d, 1H), 4.38 (s, 2H).

Example 5A

4-[5-(6-Aminopyridin-2-yl)-1,2,4-oxadiazol-3-yl] benzosulfonyl Chloride

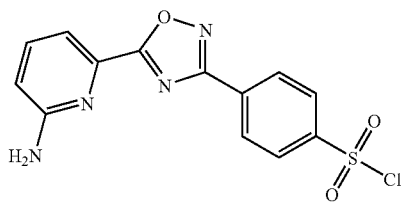

6-{3-[4-(Benzylthio)phenyl]-1,2,4-oxadiazol-5-yl}pyridin-2-amine (35.95 g) is cooled to 5° C. in a mixture of acetic acid (200 ml) and water (100 ml) in an ice bath. Chlorine is introduced gradually until the starting material has reacted completely (monitoring by HPLC) whereby the temperature must not exceed 10° C. The reaction mixture is stirred at 5° C. for 15 min and then diluted with ice water (200 ml). The crude product is collected by filtration, washed with ice water (three times) and diethylether (three times) and subsequently dried under vacuum. 26.00 g (85% of theory) of product are obtained as a solid.

LC-MS (Method 3): $R_t$=2.22 min

MS (ESI): m/z=337 [M+H]$^+$

Example 6A

2-Chloro-5-fluoro-1,3-dinitrobenzene

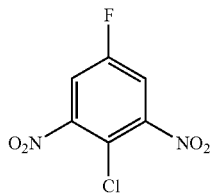

DMF (10 ml) and thionyl chloride (14 ml) are added successively to 4-fluoro-2,6-dinitrophenol (26.00 g) in benzene (50 ml). The resulting solution is stirred at room temperature for 5 min (an intermediate precipitates) and then heated under reflux for 1.5 h (or until the starting material has reacted completely). The reaction mixture is cooled to room temperature, concentrated and the residue is poured onto ice/water. The precipitate is collected by filtration, washed three times with water and dried. After recrystallization from ethanol 23.50 g (83% of theory) of product are obtained in crystalline form.

$^1$H-NMR (400 MHz, DMSO-d$_6$): δ=8.56 (d, 2H).

Example 7A

5-Fluoro-1,3-aminobenzene

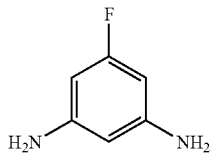

Triethylamine (12.6 ml) and palladium (10% on carbon) (6.0 g) are added to 2-chloro-5-fluoro-1,3-dinitrobenzene (10.00 g) in methanol (450 ml). The reaction mixture is hydrogenated at room temperature under a hydrogen pressure of 3 bar until the starting material has reacted completely (2 h). The batch is filtered through celite and concentrated. The residue is taken up in DCM (150 ml) and treated with a 10% citric acid solution. The aqueous phase is subsequently adjusted to a basic pH with a 2N sodium hydroxide solution and extracted with DCM (three times with 100 ml each). The organic phase is dried over sodium sulfate and concentrated. 5.0 g (88% of theory) of product are obtained as an oil.

LC-MS (Method 4): $R_t$=0.58 min

MS (ESI): m/z=127 [M+H]$^+$

Example 8A

N-(3-Amino-5-fluorophenyl)-1-cyanocyclopropanecarboxamide

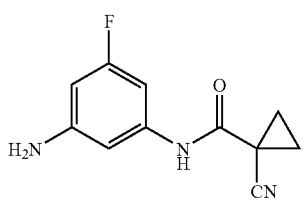

1,1-Carbonyldiimidazole (3.29 g) is added to 1-cyanocyclopropanecarboxylic acid (2.05 g) in THF and the resulting solution is stirred at room temperature for 45 min. 5-Fluoro-1,3-aminobenzene (3.00 g) is added and the mixture is stirred for a further 2.5 h. Subsequently, the reaction solution is concentrated, the residue is taken up in DCM (150 ml) and washed with water. The aqueous phase is extracted twice with DCM. The organic extracts are pooled, dried over sodium sulfate and concentrated. The residue is chromatographed on silica gel (eluent DCM to DCM-methanol 50:1). After concentrating the relevant fraction 2.35 g (58% of theory) of product are isolated.

LC-MS (Method 1): $R_t$=1.31 min

MS (ESI): m/z=220 [M+H]$^+$

Example 9A

N-(3-{[(4-Cyanophenyl)sulfonyl]amino}phenyl)acetamide

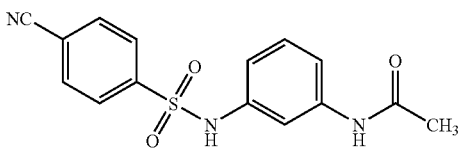

3'-Aminoacetanilide (13.54 g) is dissolved in 2-propanol (200 ml) and a solution of sodium acetate (8.51 g) in water (100 ml) is added at room temperature. 4-Cyanobenzosulfonyl chloride (20.0 g) is added, the reaction mixture is heated to 30° C. and stirred at room temperature for 3 h. The batch is poured onto ice (250 ml), the resulting solid is collected by filtration, washed with water (three times) and then dried in a drying oven. 27.8 g (98% of theory) of product are obtained as a solid.

LC-MS (Method 1): $R_t$=1.79 min
MS (ESI): m/z=316 [M+H]$^+$
$^1$H-NMR (400 MHz, DMSO-d$_6$): δ=10.52 (s, 1H), 9.94 (s, 1H), 8.05 (d, 2H), 7.90 (d, 2H), 7.46 (s, 1H), 7.27 (d, 1H), 7.13 (t, 1H), 6.72 (d, 1H), 2.00 (s, 3H).

Example 10A

N-{3-[({4-[(Z)-Amino(hydroxyimino)methyl]phenyl}sulfonyl)amino]phenyl}acetamide

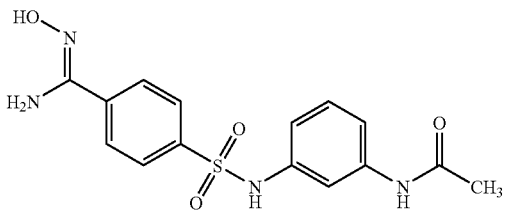

N-(3-{[(4-Cyanophenyl)sulfonyl]amino}phenyl)acetamide (27.00 g) is provided in ethanol (190 ml), and hydroxylamine hydrochloride (7.14 g) and triethylamine (14.0 ml) are added successively. The reaction mixture is stirred at 50° C. for 2 h and subsequently poured onto ice, collected by filtration and dried in a vacuum cabinet. 25.78 g (86% of theory) of product are obtained as a solid.

LC-MS (Method 1): $R_t$=1.14 min
MS (ESI): m/z=349 [M+H]$^+$

Example 11A

N-(6-{3-[4-({[3-(Acetylamino)phenyl]amino}sulfonyl)phenyl]-1,2,4-oxadiazol-5-yl}pyridin-2-yl)acetamide

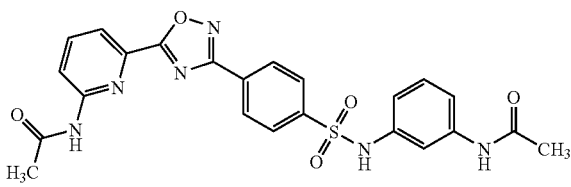

1,1-Carbonyldiimidazole (9.78 g) dissolved in dioxane (100 ml) is added dropwise to 6-acetylaminopyridine-2-carboxylic acid (10.86 g) in a mixture of dioxane (100 ml) and DMF (60 ml) and the mixture is stirred at room temperature for 3 h. N-{3-[({4-[(Z)-Amino(hydroxyimino)methyl]phenyl}sulfonyl)amino]phenyl}acetamide is then added as a solid and the reaction mixture is stirred at room temperature for 16 h. Subsequently, the reaction mixture is stirred at 100° C. for 4 h and then poured onto ice/water. The product is left to stand for 10 min, collected by filtration, washed with water (three times) and dried in a vacuum oven. 25.55 g (90% of theory) of product are obtained as a solid.

HPLC (Method 5): $R_t$=4.03 min
MS (ESI): m/z=493 [M+H]$^+$

Example 12A

N-(3-Aminophenyl)-4-[5-(6-aminopyridin-2-yl)-1,2,4-oxadiazol-3-yl]benzosulfonamide

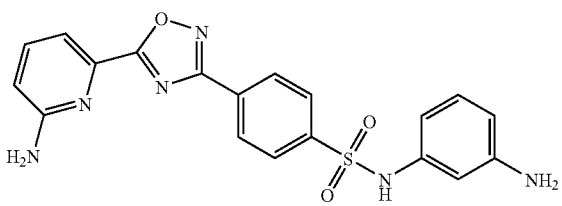

15% hydrochloric acid (150 ml) is added to N-(6-{3-[4-({[3-(acetylamino)phenyl]amino}sulfonyl)phenyl]-1,2,4-oxadiazol-5-yl}pyridin-2-yl)acetamide (20.00 g) in ethanol (200 ml). The reaction mixture is stirred under reflux for 6 h and the pH is subsequently adjusted in the heat to pH 4 using a 10% sodium hydroxide solution. The reaction mixture is cooled to 5° C. and stirred for 16 h. The crude product is collected by suction filtration, washed with water (twice) and subsequently dried. 12.73 g (77% of theory) of product are obtained as a solid.

HPLC (Method 5): $R_t$=3.53 min
MS (ESI): m/z=409 [M+H]$^+$
$^1$H-NMR (300 MHz, DMSO-d$_6$): δ=10.16 (br s, 1H), 8.23 (d, 2H), 7.97 (d, 2H), 7.63 (t, 1H), 7.45 (d, 1H), 6.85 (t, 1H), 6.74 (d, 1H), 6.58 (br s, 2H), 6.42 (s, 1H), 6.28 (t, 1H), 5.44 (br s, 2H).

Example 13A

N-(6-Bromopyridin-2-yl)acetamide

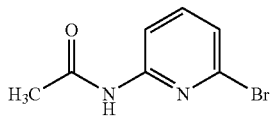

2-Amino-6-bromopyridine (5.40 g) and acetyl chloride (2.66 ml) are provided in methylene chloride (80 ml) and cooled to 0° C. Triethylamine (6.53 ml) is then added dropwise and the mixture is subsequently warmed to room temperature while stirring. A 10% sodium hydrogen carbonate solution is added to the batch and the batch is extracted with methylene chloride. The organic phase is washed with water and a saturated sodium chloride solution, dried over sodium sulfate and concentrated. After flash chromatography (eluent methylene chloride/methanol 1:0, 500:1) 5.84 g (86% of theory) of product are obtained.

HPLC (Method 6): R$_t$=3.66 min

MS (DCI/NH$_3$): m/z=215 and 217 [M+H]$^+$, 232 and 234 [M+NH$_4$]$^+$, 249 and 251 [M+NH$_4$+NH$_3$]$^+$ $^1$H-NMR (400 MHz, DMSO-d$_6$): δ=10.79 (s, 1H, NH), 8.08 (d, 1H), 7.71 (t, 1H), 7.31 (d, 1H), 2.09 (s, 3H).

Example 14A

N-[6-(3-Hydroxy-3-methylbut-1-yn-1-yl)pyridin-2-yl]acetamide

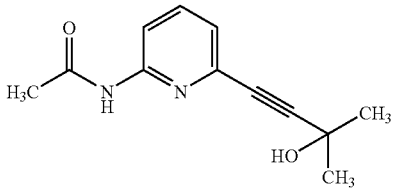

N-(6-Bromopyridin-2-yl)acetamide (5.84 g) is provided in diethylamine (50 ml). After the addition of 2-methyl-3-butyn-2-ol (2.51 g), bis(triphenylphosphine)palladium(II) chloride (381 mg) and copper(I) iodide (52 mg) the mixture is stirred at room temperature for 2 h. The batch is then concentrated and flash-chromatographed (eluent methylene chloride/methanol 200:1, 100:1, 50:1). 5.20 g (88% of theory) of product are obtained.

HPLC (Method 6): R$_t$=3.30 min

MS (Method M-40, DCI/NH$_3$): m/z=219 [M+H]$^+$ $^1$H-NMR (400 MHz, DMSO-d$_6$): δ=10.68 (s, 1H, NH), 8.05 (d, 1H), 7.75 (t, 1H), 7.14 (d, 1H), 5.55 (s, 1H, OH), 2.07 (s, 3H), 1.46 (s, 6H).

Example 15A

N-(6-Ethynylpyridin-2-yl)acetamide

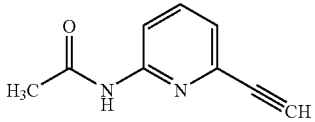

N-[6-(3-Hydroxy-3-methylbut-1-yn-1-yl)pyridin-2-yl]acetamide (5.20 g) is provided in toluene (50 ml), sodium hydride (95 mg) is added and the mixture is stirred at 120° C. for 1.5 h. The batch is concentrated, the residue diluted with water and extracted with ethyl acetate. The organic phase is dried over sodium sulfate, concentrated and flash-chromatographed (eluent methylene chloride/methanol 1:0, 500:1, 200:1, 100:1). 1.75 g (43% of theory) of product are obtained.

HPLC (Method 6): R$_t$=3.18 min

MS (Method M-40, DCI/NH$_3$): m/z=161 [M+H]$^+$, 178 [M+NH$_4$]$^+$, $^1$H-NMR (400 MHz, DMSO-d$_6$): δ=10.68 (s, 1H, NH), 8.10 (d, 1H), 7.78 (t, 1H), 7.26 (d, 1H), 4.31 (s, 1H), 2.08 (s, 3H).

Example 16A

N-(3-{[(4-Iodophenyl)sulfonyl]amino}phenyl)acetamide

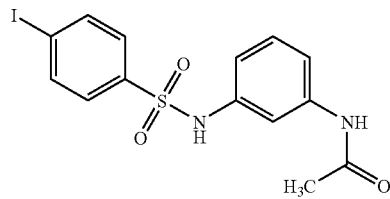

4-Iodobenzylsulfonyl chloride (10.0 g) is provided in isopropanol (100 ml), sodium acetate (3.12 g), which is dissolved in a little water, is added and the mixture is stirred at room temperature for 30 min. N-(3-Aminophenyl)acetamide (4.96 g) is then added and the mixture is further stirred over night. The batch is diluted with water and a saturated sodium chloride solution and extracted with ethyl acetate. The organic phase is dried over sodium sulfate, concentrated and flash-chromatographed (eluent methylene chloride/methanol 1:0, 100:1, 80:1). 9.62 g (70% of theory) of product are obtained.

HPLC (Method 6): R$_t$=4.14 min

MS (ES$^+$, ES$^-$): m/z=417 [M+H]$^+$, 415 [M−H]$^-$, $^1$H-NMR (400 MHz, DMSO-d$_6$): δ=10.31 (s, 1H, NH), 9.91 (s, 1H, NH), 7.93 (d, 2H), 7.51 (d, 2H), 7.45 (s, 1H), 7.26 (d, 1H), 7.12 (t, 1H), 6.73 (d, 1H), 2.00 (s, 3H).

Example 17A

N-(6-{[4-({[3-(Acetylamino)phenyl]amino}sulfonyl)phenyl]ethynyl}pyridin-2-yl)acetamide

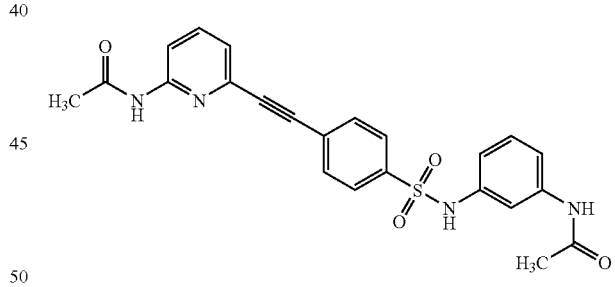

N-(3-{[(4-Iodophenyl)sulfonyl]amino}phenyl)acetamide (4.60 g), tetrakis(triphenylphosphine)palladium(0) (1.28 g) and copper(I) iodide (421 mg) are provided in DMF under an argon atmosphere, N-(6-ethynylpyridin-2-yl)acetamide (2.66 g) and triethylamine (15.4 ml) are added and the mixture is stirred at room temperature for 2 h. The mixture in then diluted with water, extracted into methylene chloride and the organic phase is dried and flash-chromatographed (eluent methylene chloride/methanol 1:0, 200:1, 100:1, 50:1, 30:1). 3.56 g (48% of theory) of product are obtained.

HPLC (Method 6): R$_t$=3.86 min

MS (ES$^+$, ES$^-$): m/z=449 [M+H]$^+$, 447 [M−H]$^-$, $^1$H-NMR (400 MHz, DMSO-d$_6$): δ=10.76 (s, 1H, NH), 10.38 (s, 1H, NH), 9.93 (s, 1H, NH), 8.13 (d, 1H), 7.88-7.78 (m, 3H), 7.73 (d, 2H), 7.48 (s, 1H), 7.37 (d, 1H), 7.26 (d, 1H), 7.12 (t, 1H), 6.76 (d, 1H), 2.09 (s, 3H), 2.00 (s, 3H).

Example 18A

N-(3-Aminophenyl)-4-[(6-aminopyridin-2-yl)ethynyl]benzosulfonamide Dihydrochloride

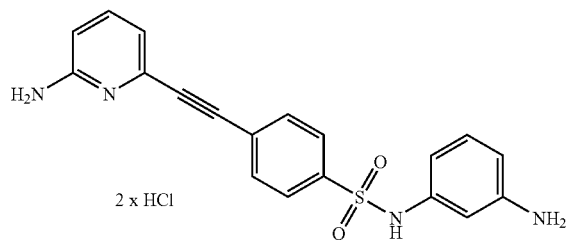

N-(6-{[4-({[3-(Acetylamino)phenyl]amino}sulfonyl)phenyl]ethynyl}pyridin-2-yl)acetamide (3.12 g) is provided in ethanol (45 ml), 20% hydrochloric acid (45 ml) is added and the mixture is stirred at 60° C. for 3 h. The batch is concentrated and the residue is stirred with acetonitrile. After collection by suction filtration, further washing with acetonitrile and drying under high vacuum, 3.45 g (quantitative) of product are obtained.

HPLC (Method 6): $R_t$=3.65 min

MS (ES$^+$, ES$^-$): m/z=365 [M+H]$^+$, 363 [M−H]$^-$, $^1$H-NMR (400 MHz, DMSO-d$_6$): δ=10.70 (s, 1H, NH), 7.91-7.78 (m, 5H), 7.24 (t, 1H), 7.09 (d, 1H), 7.02 (s, 1H), 6.96-6.83 (m, 3H).

Example 19A

4-[5-(6-Acetylaminopyridin-2-yl)-1,2,4-oxadiazol-3-yl]benzosulfonylchloride

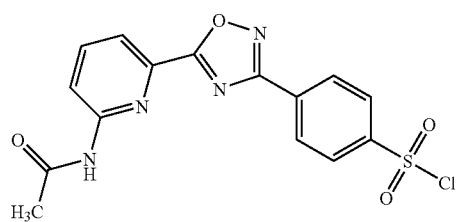

N-(6-{3-[4-(Benzylthio)phenyl]-1,2,4-oxadiazol-5-yl}pyridin-2-yl)acetamide (11.55 g) is stirred in a mixture of acetic acid (80 ml) and water (50 ml) in an ice bath and cooled to 5° C. Chlorine is introduced gradually until the starting material has reacted completely (monitoring by HPLC), whereby the temperature must not exceed 10° C. The reaction mixture is stirred at 5° C. for 15 min and then diluted with ice water (100 ml). The crude product is collected by filtration, washed with ice water (three times) and diethylether (three times) and subsequently dried under vacuum. 9.60 g (88% of theory) of product are obtained as a solid.

LC-MS (Method 3): $R_t$=2.31 min

MS (ESI): m/z=379 [M+H]$^+$

Exemplary Embodiments

Example 1

N-{3-[({4-[5-(6-Aminopyridin-2-yl)-1,2,4-oxadiazol-3-yl]phenyl}sulfonyl)amino]-5-fluorophenyl}-1-cyanocyclopropanecarboxamide

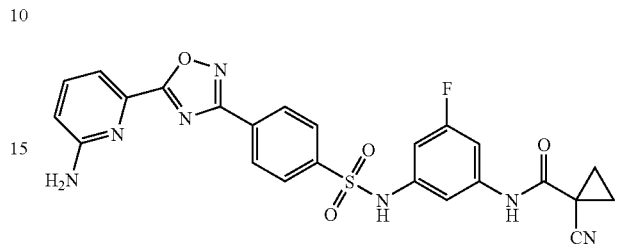

N-(3-Amino-5-fluorophenyl)-1-cyanocyclopropanecarboxamide (2.46 g) is added to 4-[5-(6-aminopyridin-2-yl)-1,2,4-oxadiazol-3-yl]benzosulfonyl chloride (3.78 g) in dry pyridine (120 ml). The resulting solution is stirred at room temperature for 18 h and subsequently poured onto ice/water. The crude product is collected by filtration, washed with water and dried. After chromatography on silica gel (methylene chloride to methylene chloride/methanol 50:1) and concentrating the relevant fractions, 2.28 g (40% of theory) of product are isolated.

LC-MS (Method 3): $R_t$=2.07 min

MS (ESI): m/z=520 [M+H]$^+$ $^1$H-NMR (400 MHz, DMSO-d$_6$): δ=8.37 (d, 2H), 8.01 (d, 2H), 7.64 (t, 1H), 7.45 (d, 1H), 7.35 (s, 1H), 7.21 (br d, 1H), 6.73 (d, 1H), 6.68 (br d, 1H), 6.56 (br s, 2H), 1.65 (s, 4H).

Example 2

N-{3-[({4-[5-(6-Aminopyridin-2-yl)-1,2,4-oxadiazol-3-yl]phenyl}sulfonyl)amino]phenyl}-1-cyanocyclopropanecarboxamide

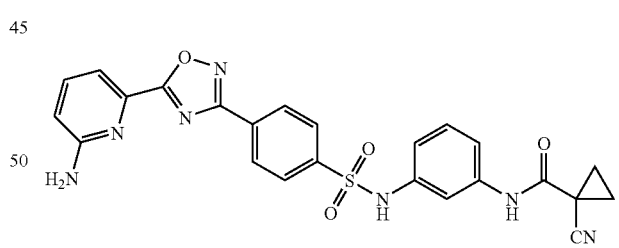

N-(3-Aminophenyl)-4-[5-(6-aminopyridin-2-yl)-1,2,4-oxadiazol-3-yl]benzosulfonamide (4.50 g) is provided in dry DMF (110 ml), HATU (6.28 g), 1-cyanocyclopropane carboxylic acid (2.45 g) and N,N-diisopropylethylamine (2.90 ml) are added and the reaction mixture is stirred under argon at room temperature for 1 h and subsequently concentrated. The residue is chromatographed on silica gel (eluent methylene chloride/methanol 100:1 to 20:1). After concentrating the relevant fractions, 4.99 g (90% of theory) of product can be isolated.

LC-MS (Method 2): $R_t$=2.13 min

MS (ESI): m/z=502 [M+H]$^+$ $^1$H-NMR (400 MHz, DMSO-d$_6$): δ=10.47 (s, 1H), 10.06 (s, 1H), 8.23 (d, 2H), 7.97 (d, 2H), 7.64 (t, 1H), 7.53 (s, 1H), 7.45 (d, 1H), 7.28 (d, 1H), 7.17 (t, 1H), 6.84 (d, 1H), 6.73 (d, 1H), 1.65 (s, 4H).

Example 3

N-{3-[({4-[5-(6-Aminopyridin-2-yl)-1,2,4-oxadiazol-3-yl]phenyl}sulfonyl)amino]-2-methylphenyl}-1-cyanocyclopropanecarboxamide

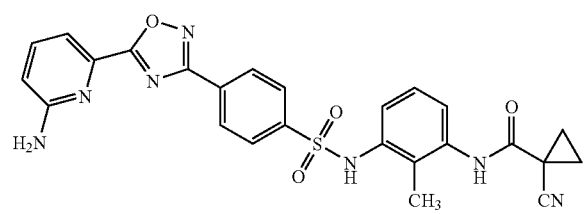

The preparation takes place in analogy to Example 2 starting from 3'-amino-2'-methylphenylacetamide.

LC-MS (Method 3): R$_t$=1.91 min

MS (ESI): m/z=516 [M+H]$^+$ $^1$H-NMR (400 MHz, DMSO-d$_6$): δ=9.91 (s, 1H), 9.67 (s, 1H), 8.26 (d, 2H), 7.87 (d, 2H), 7.65 (t, 1H), 7.47 (d, 1H), 7.10 (m, 2H), 6.84 (dd, 1H), 6.76 (d, 1H), 1.91 (s, 3H), 1.63 (m, 4H).

Example 4

N-{3-[({4-[(6-Aminopyridin-2-yl)ethynyl]phenyl}sulfonyl)amino]phenyl}-1-cyanocyclopropanecarboxamide Hydrochloride

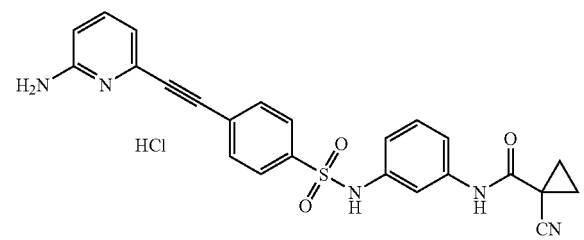

N-(3-Aminophenyl)-4-[(6-aminopyridin-2-yl)ethynyl]benzosulfonamide dihydrochloride (750 mg), 1-cyanocyclopropionic acid (229 mg), HATU (783 mg) and N,N-diisopropylethylamine (1.04 ml) are stirred over night at room temperature in dry DMF (7 ml). The batch is purified directly by preparative HPLC (eluent water (with 1% hydrochloric acid)/acetonitrile, flow rate 50 ml/min) and 400 mg (47% of theory) of product are obtained.

HPLC (Method 6): R$_t$=3.87 min

MS (ES$^+$, ES$^-$): m/z=458 [M−HCl+H]$^+$, 456 [M−HCl−H]$^-$,

1H-NMR (400 MHz, DMSO-d6): δ=10.45 (s, 1H, NH), 10.07 (s, 1H, NH), 7.83 (d, 2H), 7.79-7.66 (m, 3H), 7.51 (s, 1H), 7.27 (d, 1H), 7.17 (t, 1H), 7.01 (d, 1H), 6.82 (d, 2H), 1.65 (s, 4H).

Example 5

N-{3-[({4-[5-(6-Acetylaminopyridin-2-yl)-1,2,4-oxadiazol-3-yl]phenyl}sulfonyl)amino]-5-fluorophenyl}-1-cyanocyclopropanecarboxamide

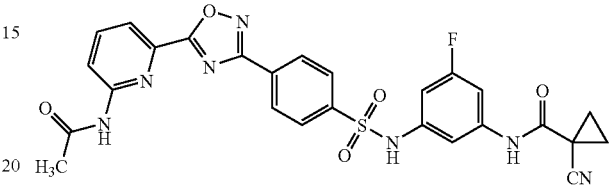

N-(3-Amino-5-fluorophenyl)-1-cyanocyclopropancarboxamide (100 mg) is added to 4-[5-(6-acetylaminopyridin-2-yl)-1,2,4-oxadiazol-3-yl]benzosulfonylchloride (148 mg) in dry pyridine (2 ml). The resulting solution is stirred at room temperature for 18 h and subsequently poured onto ice/water. The crude product is collected by filtration, washed with water and dried. After preparative RP-HPLC (eluent acetonitrile:water gradient) and concentrating the relevant fractions, 53 mg (24% of theory) of product are isolated.

LC-MS (Method 7): R$_t$=2.46 min

MS (ESI): m/z=562 [M+H]$^+$ $^1$H-NMR (400 MHz, DMSO-d$_6$): δ=10.99 (s, 1H), 10.78 (s, 1H), 10.26 (s, 1H), 8.40 (d, 1H), 8.17 (d, 2H), 8.06 (m, 4H), 7.37 (s, 1H), 7.21 (d, 1H), 6.68 (d, 1H), 2.15 (s, 3H), 1.66 (s, 4H).

B. Assessment of the Physiological Activity

The in vitro activity of the compounds of the invention can be shown in the following assays:

Anti-HCMV (Anti-Human Cytomegalovirus) Cytopathogenicity Tests

The test compounds are employed as 50 millimolar (mM) solutions in dimethyl sulfoxide (DMSO). Ganciclovir® serves as reference compound. After the addition of 2 μl of the 50, 5, 0.5 and 0.05 mM DMSO stock solutions respectively to 98 μl portions of cell culture medium in row 2 A-H for duplicate determinations, 1:2 dilutions are carried out with 50 μl portions of medium up to row 11 of the 96-well plate. The wells in rows 1 and 12 each contain 50 μl of medium. 150 μl of a suspension of 1×10$^4$ cells (human prepuce fibroblasts [NHDF]) are then pipetted into each of the wells (row 1=cell control) and, in rows 2-12, a mixture of HCMV-infected and uninfected NHDF cells (M.O.I.=0.001-0.003), i.e. 1-3 infected cells per 1000 uninfected cells. Row 12 (without substance) serves as virus control. The final test concentrations are 250-0.0005 mM. The plates are incubated at 37° C./5% CO$_2$ for 6 days, i.e. until all the cells in the virus controls are infected (100% cytopathogenic effect [CPE]). The wells are then fixed and stained by the addition of a mixture of formalin and Giemsa's dye (30 min), washed with bidistilled water and dried in a drying oven at 50° C. The plates are then assessed visually using an overhead microscope (plaque multiplier from Technomara).

The following data can be obtained from the test plates:

$CC_{50}$ (NHDF)=substance concentration in MM at which no visible cytostatic effects on the cells are evident in comparison with the untreated cell control;

$EC_{50}$ (HCMV)=substance concentration in MM which inhibits the CPE (cytopathic effect) by 50% in comparison with the untreated virus control;

SI (selectivity index)=$CC_{50}$ (NHDF)/$EC_{50}$ (HCMV).

Representative in vitro activity data for the compounds of the invention are shown in Table A:

TABLE A

| Example No. | NHDF $CC_{50}$ [µM] | HCMV $EC_{50}$ [µM] | SI HCMV |
|---|---|---|---|
| 1 | 71 | 0.011 | 6450 |
| 2 | 141 | 0.007 | 20140 |
| 3 | 102 | 0.002 | 51000 |
| 4 | 47 | 0.021 | 2240 |
| 5 | 71 | 0.026 | 2730 |

The suitability of the compounds of the invention for the treatment of HCMV infections can be shown in the following animal model:

HCMV Xenograft Gelfoam® Model

Animals:

5-6-week-old immunodeficient mice (16-20 g), Fox Chase SCID.NOD or NOD.CB17-Prkdc/J, are obtained from commercial breeders (Taconic M&B, Denmark; Jackson, USA). The animals are kept under sterile conditions (including bedding and feed) in isolators.

Virus Growing:

Human cytomegalovirus (HCMV), Davis or AD169 strain, is grown in vitro on human embryonic prepuce fibroblasts (NHDF cells). After the NHDF cells have been infected with a multiplicity of infection (M.O.I.) of 0.01-0.03, the virus-infected cells are harvested 5-10 days later and stored in the presence of minimal essential medium (MEM), 20% foetal calf serum (FCS) (v/v), 1% glutamine (v/v), 1% Pen/Strep (v/v) with 10% DMSO at −80° C. After serial ten-fold dilution of the virus-infected cells, the titre is determined on 24-well plates of confluent NHDF cells after fixing and staining with a Giemsa formaldehyde solution.

Preparation of the Sponges, Transplantation, Treatment and Evaluation:

Collagen sponges 1×1×1 cm in size (Gelfoam®; Peasel & Lorey, order no. 407534; K. T. Chong et al., Abstracts of 39th Interscience Conference on Antimicrobial Agents and Chemotherapy, 1999, p. 439) are initially wetted with phosphate-buffered saline (PBS), the trapped air bubbles are removed by degassing, and then stored in MEM, 10% FCS (v/v), 1% glutamine (v/v), 1% Pen/Strep (v/v). $1×10^6$ virus-infected NHDF cells (infection with HCMV Davis or HCMV AD169 M.O.I=0.03) are detached 3 hours after infection and added dropwise in 20 µl of MEM, 10% FCS (v/v), 1% glutamine (v/v), 1% Pen/Strep (v/v) onto a moist sponge. The sponges are incubated for 3 to 4 hours to allow the cells to adhere. Subsequently, after the addition of medium (MEM, 10% FCS) (v/v), 1% glutamine (v/v), 1% Pen/Strep (v/v)), the sponges are incubated over night. For the transplantation, the immunodeficient mice are anaesthetized with Avertin or a ketamine/xylazine/azepromazine mixture, the fur on the back is removed using a shaver, the epidermis is opened 1-2 cm, unstressed and the moist sponges are transplanted under the dorsal skin. The surgical wound is closed with tissue glue or clips. 4-6 hours after the transplantation, the mice can be treated for the first time (on the day of the operation one treatment is given). On subsequent days, treatment with the substance is carried out orally three times a day (7.00 h and 14.00 h and 19.00 h), twice a day (8 h and 18 h) or once a day (9 h) over a period of 8 days. The daily dose is for example 1 or 3 or 10 or 30 or 100 mg/kg of body weight, the volume administered is 10 ml/kg of body weight. The substances are formulated in the form of a 0.5% tylose suspension/PBS with 2% DMSO or another suitable mixture aiding the solubility of the substances, e.g. 2% ethanol, 2.5% solutol, 95.5% PBS. 10 days after transplantation and about 16 hours after the last administration of substance, the animals are sacrificed painlessly and the sponge is removed. The virus-infected cells are released from the sponge by collagenase digestion (330 U/1.5 ml) and stored in the presence of MEM, 10% FCS (v/v), 1% glutamine (v/v), 1% Pen/Strep (v/v), 10% DMSO at −140° C. Evaluation takes place after serial ten-fold dilution of the virus-infected cells by determining the titre on 24-well plates of confluent NHDF cells after fixing and staining with a Giemsa formaldehyde solution. The number of infected cells or infectious virus particles (infectious center assay) after the substance treatment compared with the placebo-treated control group is determined. Statistical evaluation takes place by suitable computer programs, such as GraphPad Prism.

Pharmacokinetical Investigations

The pharmacokinetics of the active substances are investigated after intravenous or oral administration of doses in the range from 1 mg/kg intravenously and 3 mg/kg orally to three male Wistar rats per administration route. In order to make a repeated removal of blood possible a catheter is implanted into the jugular vein of the animals on the day before the experiment. The substances are administered intravenously as well as orally as a solution. Thereby, in most cases a plasma formulation (rat plasma with 1-2% ethanol or DMSO, 2 ml/kg) is used for the intravenous administration and a PEG formulation (10% ethanol, 40% PEG 400, 50% water, 5 ml/kg) is used for the oral administration.

After the administration of the active substance blood samples are collected over 24 h via the catheter into heparin-containing sample tubes. Subsequently to the removal of blood the blood samples are centrifuged and the plasma supernatant is pipetted into Eppendorf tubes. The plasma samples are stored at least −15° C. until the analysis takes place.

For the work-up the samples are thawed. The plasma proteins are subsequently precipitated by the addition of acetonitrile which comprises an internal standard. As internal standard a substance from the same structural class is selected which is structurally as similar as possible to the active compound. For the preparation of calibration samples different concentrations of the active substance are added to aliquots of empty plasma and these are worked up together with the unknown samples. Additionally quality control samples with three different concentrations are prepared which serve to validate the analytical procedure.

The determination of the active substance in the samples takes place by high performance liquid chromatography with mass spectrometrical detection (LC/MS-MS). The active substance concentrations in the unknown samples are determined based on their relative peak heights or areas compared to the calibration curve using the program Concalc for Windows (CCW, Integrierte Labordatensysteme, version 2.5 or later, Bayer AG). Subsequently, the pharmacokinetical parameters are calculated from the plasma concentration development over time individualized to an animal using non-compartmental analysis with the aid of the program KINCALC, version 2.50.02 (Bayer AG, 2001).

Compounds which show the desired improved pharmacokinetical profile in the rat are subsequently subjected to a pharmacokinetical investigation after administration to mice and dogs. Based on all this data, a first estimate of the human pharmacokinetics is performed by an interspecies upscaling according to Boxenbaum.

The following data can be acquired from these tests:

$V_{ss}$=distribution volume;
CL=speed of elimination;
$t_{1/2}$=half-life;
AUC=total area under the drug-concentration over time curve;
$C_{max}$=maximum concentration;
F=bioavailability;

Pharmacokinetical data for the compound of example 1 after a single intravenous and oral administration to male Wistar rats (n=3 per time point or n=3, resp.) are displayed in Table B. The compounds of the invention show an improved pharmacokinetical behaviour.

TABLE B

| Wistar rat | | |
|---|---|---|
| Dose intravenous | | 1.3 mg/kg i.v.[1] |
| $V_{ss}$ | [l/kg] | 0.321 |
| $CL_{Plasma}$ | [l/(h · kg)] | 0.064 |
| $CL_{Blood}$ | [l/(h · kg)] | 0.128 |
| $t_{1/2}$ | [h] | 4.26 |
| Dose oral | | 3 mg/kg p.o.[2] |
| $AUC_{norm,p.o.}$ | [kg · h/l] | 8.58 |
| $C_{max, norm, p.o.}$ | [kg/l] | 1.08 |
| F | [%] | 55.3 |

[1]solution in rat plasma with 1% DMSO, 2 ml/kg
[2]solution in 10% ethanol, 40% PEG 400, 50% water, 5 ml/kg Identification of Metabolites Species differences in the metabolism of an active compound can have a large influence on its developability. It is an aim to find substances which do not differ significantly in the metabolic degradation pathways between humans and usual tox species such as for example rat and dog. For this new active substances are first incubated in vitro with liver microsomes of rat, dog and human in order to compare the phase I metabolism. Subsequently, the still interesting compounds are additionally incubated in hepatocytes of rat and human in order to obtain a complete hepatic phase I and phase II metabolism and to compare it.

All new active compounds are incubated in a concentration of 20 µM. For this stock solutions with a concentration of 2 mM in acetonitrile are prepared which are then pipetted into the incubation batch with a 1:100 dilution in order to have a maximum 1% of acetonitrile in the batch. The liver microsomes are incubated at 37° C. in 50 mM potassium phosphate buffer pH 7.4 with and without NADPH-generating system, consisting of 1 mM $NADP^+$, 10 mM glucose-6-phosphate and 1 unit of glucose-6-phosphate dehydrogenase. Primary hepatocytes are also incubated at 37° C. in suspension in Williams E medium. After an incubation time of 0-4 h the incubation batches are stopped with acetonitrile (final concentration about 30%) and the protein is centrifuged off at about 15000×g. The samples stopped this way are either analyzed directly or stored at −20° C. until the analysis.

Analysis takes place using high performance liquid chromatography with ultraviolet and mass spectrometrical detection (HPLC-UV-MS). For this, the supernatants of the incubation samples are chromatographed using suitable C18 reversed phase columns and variable mixtures of acetonitrile and 10 mM ammonium formate. The UV-chromatograms in connection with the mass spectrometrical data serve to identify the metabolites. The metabolite profiles of the respective investigated species generated this way are compared and serve to identify species differences.

C. Exemplary Embodiments of Pharmaceutical Compositions

The compounds of the invention can be converted into pharmaceutical preparations in the following ways:

Tablet:

Composition:

100 mg of the compound of Example 1, 50 mg of lactose (monohydrate), 50 mg of corn starch (native), 10 mg of polyvinylpyrrolidone (PVP 25) (BASF, Ludwigshafen, Germany) and 2 mg of magnesium stearate.

Tablet weight 212 mg. Diameter 8 mm, radius of curvature 12 mm.

Production:

The mixture of active ingredient, lactose and starch is granulated with a 5% solution (m/m) of the PVP in water. The granules are then dried and mixed with the magnesium stearate for 5 min. This mixture is compressed using a conventional tablet press (see above for format of the tablet). A guideline for the compressive force used for the compression is 15 kN.

Suspension which can be Administered Orally:

Composition:

1000 mg of the compound of Example 1, 1000 mg of ethanol (96%), 400 mg of Rhodigel (Xanthan gum, FMC, Pennsylvania, USA) and 99 g of water.

10 ml of oral suspension are equivalent to a single dose of 100 mg of the compound of the invention.

Production:

The Rhodigel is suspended in ethanol and the active ingredient is added to the suspension. The water is added while stirring. The mixture is stirred for about 6 h until the swelling of the Rhodigel is complete.

Solution which can be Administered Intravenously:

Composition:

10-500 mg of the compound of Example 1, 15 g of polyethylene glycol 400 and 250 g of water for injection purposes.

Production:

The compound of Example 1 is dissolved together with polyethylene glycol 400 in the water while stirring. The solution is sterilized by filtration (pore diameter 0.22 µm) and dispensed under aseptic conditions into heat-sterilized infusion bottles. The latter are closed with infusion stoppers and crimped caps.

The invention claimed is:
1. A compound of formula

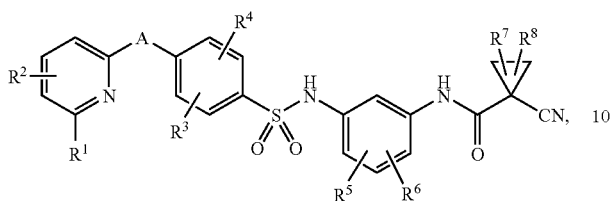
(I)

in which
A represents a group of formula

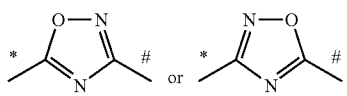
or whereby
* is the linkage site to the carbon atom of the pyridinyl ring, and
# is the linkage site to the carbon atom of the phenyl ring,
$R^1$ represents hydrogen, amino or methylcarbonylamino,
$R^2$ represents hydrogen or halogen,
$R^3$ represents hydrogen, halogen or cyano,
$R^4$ represents hydrogen, halogen or cyano,
$R^5$ represents hydrogen or halogen,
$R^6$ represents hydrogen or halogen,
$R^7$ represents hydrogen, halogen or $C_1$-$C_3$-alkyl, and
$R^8$ represents hydrogen, halogen or $C_1$-$C_3$-alkyl,
or one of its salts.

2. The compound of claim 1, whereby
A represents a group of formula

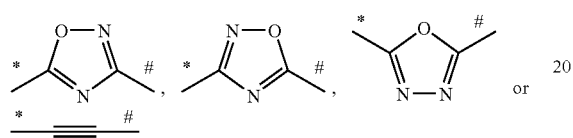

whereby
* is the linkage site to the carbon atom of the pyridinyl ring, and
# is the linkage site to the carbon atom of the phenyl ring,
$R^1$ represents hydrogen, amino or methylcarbonylamino,
$R^2$, $R^3$ and $R^4$ each represent hydrogen,
$R^5$ represents hydrogen or halogen,
$R^6$ represents hydrogen or halogen, and
$R^7$ and $R^8$ each represent hydrogen,
or one of its salts.

3. The compound of claim 1, whereby
A represents a group of formula

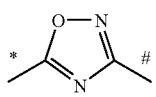

whereby
* is the linkage site to the carbon atom of the pyridinyl ring, and
# is the linkage site to the carbon atom of the phenyl ring,
$R^1$ represents amino or methylcarbonylamino,
$R^2$, $R^3$ and $R^4$ each represent hydrogen,
$R^5$ represents hydrogen,
$R^6$ represents hydrogen or halogen, and
$R^7$ and $R^8$ each represent hydrogen,
or one of its salts.

4. A method for the preparation of a compound of formula (I) of claim 1, comprising reacting a compound of formula

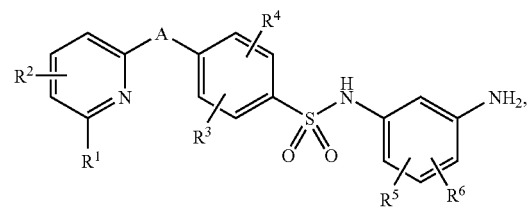
(II)

in which
A, $R^1$, $R^2$, $R^3$, $R^4$, $R^5$ and $R^6$ have the meaning indicated in claim 1, with a compound of formula

(III)

in which
$R^7$ and $R^8$ have the meaning indicated in claim 1, and
$X^1$ represents halogen or hydroxy.

5. A medicament comprising a therapeutically effective amount of a compound of claim 1 in combination with an inert, non-toxic, pharmaceutically acceptable excipient.

6. A method for the production of a medicament for the treatment of viral infections, comprising mixing a therapeutically effective amount of a compound of claim 1 with at least one pharmaceutically acceptable excipient, wherein the viral infection is an infection with the human cytomegalovirus (HCMV) or another representative of the group of herpes viridae.

7. A method of controlling viral infections in humans and animals by administering an antivirally effective amount of at least one compound of claim 1, wherein the viral infection is an infection with the human cytomegalovirus (HCMV) or another representative of the group of herpes viridae.

8. The method of claim 4, wherein $X^1$ is chlorine, bromine, or hydroxy.

* * * * *